(12) United States Patent
Kishine et al.

(10) Patent No.: US 9,933,369 B2
(45) Date of Patent: Apr. 3, 2018

(54) METHOD FOR MEASURING CONCENTRATION OF DISSOLVED SUBSTANCE

(71) Applicant: KURITA WATER INDUSTRIES LTD., Tokyo (JP)

(72) Inventors: Yoshitaka Kishine, Tokyo (JP); Toshikazu Takahashi, Tokyo (JP); Junichi Takahashi, Tokyo (JP)

(73) Assignee: KURITA WATER INDUSTRIES LTD., Tokyo (JP)

(*) Notice: Subject to any disclaimer, the term of this patent is extended or adjusted under 35 U.S.C. 154(b) by 0 days.

(21) Appl. No.: 14/764,817

(22) PCT Filed: Feb. 13, 2014

(86) PCT No.: PCT/JP2014/053244
§ 371 (c)(1),
(2) Date: Jul. 30, 2015

(87) PCT Pub. No.: WO2014/129365
PCT Pub. Date: Aug. 28, 2014

(65) Prior Publication Data
US 2015/0362436 A1 Dec. 17, 2015

(30) Foreign Application Priority Data

Feb. 22, 2013 (JP) ................. 2013-033463
Feb. 5, 2014 (JP) ................. 2014-019902

(51) Int. Cl.
*G01N 21/78* (2006.01)
*G01N 21/27* (2006.01)
*G01N 21/31* (2006.01)

(52) U.S. Cl.
CPC ............. *G01N 21/78* (2013.01); *G01N 21/27* (2013.01); *G01N 21/31* (2013.01)

(58) Field of Classification Search
CPC ........ G01N 21/78; G01N 21/77; G01N 21/75; G01N 21/00; G01N 21/31; G01N 21/25; G01N 21/17
(Continued)

(56) References Cited

U.S. PATENT DOCUMENTS

2002/0167663 A1 11/2002 Martino et al.

FOREIGN PATENT DOCUMENTS

| JP | H10-332583 A | 12/1998 |
|----|--------------|---------|
| JP | H11-344382 A | 12/1999 |

(Continued)

OTHER PUBLICATIONS

English Marchine Translation of Application No, JP 2008-32987, same as Foreign Document No. JP 2010151605 A, A Description and Claims, submitted on IDS on Jul. 30, 2015, obtained on Oct. 30, 2015.*

(Continued)

*Primary Examiner* — Christine T Mui
(74) *Attorney, Agent, or Firm* — Manabu Kanesaka

(57) ABSTRACT

A reagent includes a coloring agent allowing a measured solution to develop a color transmitting a region component light for a dissolved-substance concentration measurement selected from three region component lights of red, green, and blue obtained by transmitting a light including a visible light region to the measured solution colored by addition of the reagent to the sample, and dividing a light of the visible light region of a transmitted light thereof into roughly three portions. Based on the transmitted light from the measured solution with the coloring agent added, an absorbance of the region component light for the dissolved-substance concentration measurement, and an absorbance A3 of another region component light resulted only from the coloring agent are calculated. Whether or not the reagent in a nec- (Continued)

essary quantity is added to the sample can be judged by comparing the absorbance A3 and a standard absorbance A0.

6 Claims, 9 Drawing Sheets

(58) Field of Classification Search
USPC .................................................. 436/166, 164
See application file for complete search history.

(56) References Cited

FOREIGN PATENT DOCUMENTS

| JP | 2010-050891 A | | 2/2001 | |
|----|---------------|---|--------|---|
| JP | 2008-161804 A | | 7/2008 | |
| JP | 2010-151605 A | | 7/2010 | |
| JP | 2010-181150 | * | 8/2010 | ............ G01N 21/27 |
| JP | 2010-181150 A | | 8/2010 | |

OTHER PUBLICATIONS

English Machine Translation of JP 2010-181150.*
Takahashi J. English Translation of JP 2010 181150 Abstract, Claims and Description, obtained on Mar. 15, 2017, pp. 1-42.*
Takahashi J. English Translation of JP 2010 151605 from Espacenet, Description, obtained on Mar. 15, 2017, pp. 1-28.*
PCT, "International Search Report for International Application No. PCT/JP2014/053244" dated May 2014.

* cited by examiner

| WELLCLEAN Concentration (mg/L) | Absorbance by Concentration Measuring Apparatus | | |
|---|---|---|---|
| | Red Region Component Light | Green Region Component Light | Blue Region Component Light |
| 0 | 0.000 | 0.000 | 0.000 |
| 20 | 0.021 | 0.026 | 0.033 |
| 40 | 0.046 | 0.057 | 0.066 |
| 60 | 0.075 | 0.093 | 0.099 |
| 80 | 0.106 | 0.135 | 0.131 |
| 100 | 0.145 | 0.183 | 0.164 |

FIG. 6A

Addition Quantity of Reagent Including Coloring Agent : 0.2 mL

| WELLCLEAN Concentration (mg/L) | Absorbance by Concentration Measuring Apparatus | | | Sum of Absorbances of Red and Green, Two Region Component Lights | | |
|---|---|---|---|---|---|---|
| | Red Region Component Light A | Green Region Component Light B | Blue Region Component Light C | Resulted from WELLCLEAN and Coloring Agent D=A+B | Resulted Only from WELLCLEAN E | Resulted Only from Coloring Agent F=D−E |
| 0 | 0.044 | 0.040 | 0.000 | 0.084 | 0.000 | 0.084 |
| 20 | 0.065 | 0.066 | 0.033 | 0.131 | 0.047 | 0.084 |
| 40 | 0.090 | 0.097 | 0.066 | 0.187 | 0.103 | 0.084 |
| 60 | 0.119 | 0.133 | 0.099 | 0.252 | 0.168 | 0.084 |
| 80 | 0.152 | 0.175 | 0.132 | 0.327 | 0.241 | 0.084 |
| 100 | 0.189 | 0.223 | 0.165 | 0.412 | 0.328 | 0.084 |

FIG. 6B

Addition Quantity of Reagent Including Coloring Agent : 0.1 mL

| WELLCLEAN Concentration (mg/L) | Absorbance by Concentration Measuring Apparatus | | | Sum of Absorbances of Red and Green, Two Region Component Lights | | |
|---|---|---|---|---|---|---|
| | Red Region Component Light A | Green Region Component Light B | Blue Region Component Light C | Resulted from WELLCLEAN and Coloring Agent D=A+B | Resulted Only from WELLCLEAN E | Resulted Only from Coloring Agent F=D−E |
| 0 | 0.022 | 0.020 | 0.000 | 0.042 | 0.000 | 0.042 |
| 20 | 0.043 | 0.046 | 0.033 | 0.089 | 0.047 | 0.042 |
| 40 | 0.068 | 0.077 | 0.066 | 0.145 | 0.103 | 0.042 |
| 60 | 0.097 | 0.113 | 0.099 | 0.210 | 0.168 | 0.042 |
| 80 | 0.130 | 0.155 | 0.132 | 0.285 | 0.243 | 0.042 |
| 100 | 0.167 | 0.203 | 0.164 | 0.370 | 0.328 | 0.042 |

FIG. 6C

Addition Quantity of Reagent Including Coloring Agent : 0.05 mL

| WELLCLEAN Concentration (mg/L) | Absorbance by Concentration Measuring Apparatus | | | Sum of Absorbances of Red and Green, Two Region Component Lights | | |
|---|---|---|---|---|---|---|
| | Red Region Component Light A | Green Region Component Light B | Blue Region Component Light C | Resulted from WELLCLEAN and Coloring Agent D=A+B | Resulted Only from WELLCLEAN E | Resulted Only from Coloring Agent F=D−E |
| 0 | 0.011 | 0.010 | 0.000 | 0.021 | 0.000 | 0.021 |
| 20 | 0.032 | 0.036 | 0.033 | 0.068 | 0.047 | 0.021 |
| 40 | 0.057 | 0.067 | 0.066 | 0.124 | 0.103 | 0.021 |
| 60 | 0.071 | 0.084 | 0.082 | 0.155 | 0.134 | 0.021 |
| 80 | 0.071 | 0.084 | 0.082 | 0.155 | 0.134 | 0.021 |
| 100 | 0.071 | 0.084 | 0.082 | 0.155 | 0.134 | 0.021 |

FIG. 7

| Addition Quantity of Reagent Including Coloring Agent (mL) | Absorbance by Concentration Measuring Apparatus | | | Sum of Absorbances of Red and Green, Two Region Component Lights Resulted Only from Coloring Agent |
|---|---|---|---|---|
| | Blue Region Component Light | Red Region Component Light | Green Region Component Light | |
| 0.05 | 0.000 | 0.011 | 0.010 | 0.021 |
| 0.10 | 0.001 | 0.022 | 0.020 | 0.042 |
| 0.15 | 0.001 | 0.033 | 0.030 | 0.063 |
| 0.20 | 0.002 | 0.044 | 0.040 | 0.084 |
| 0.25 | 0.002 | 0.055 | 0.050 | 0.105 |
| 0.30 | 0.003 | 0.066 | 0.060 | 0.126 |

FIG. 8

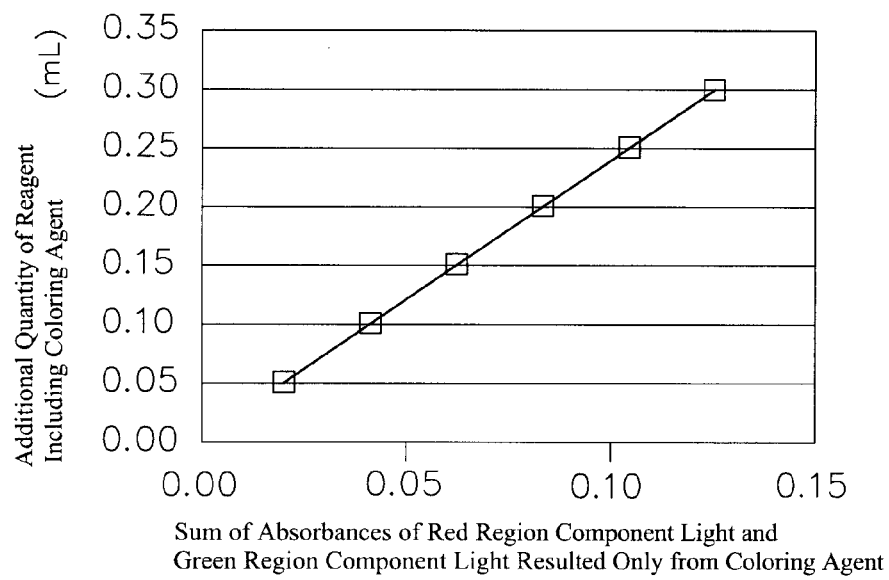

Sum of Absorbances of Red Region Component Light and Green Region Component Light Resulted Only from Coloring Agent

| Absorbance of Red Region Component Light | Absorbance of Green Region Component Light | Concentration of Measured Dissolved Substance |
|---|---|---|
| 0.7 |  | 5 |
| 0.6 | 0.01 | 10 |
| 0.5 | 0.01 | 15 |
| 0.4 | 0.01 | 20 |
| 0.3 | 0.1 | 25 |
| 0.2 | 0.2 | 30 |
| 0.1 | 0.3 | 35 |
| 0.05 | 0.4 | 40 |
| 0.02 | 0.5 | 45 |
| 0.01 | 0.6 | 50 |
|  | 0.7 | 55 |

METHOD FOR MEASURING CONCENTRATION OF DISSOLVED SUBSTANCE

RELATED APPLICATIONS

The present application is National Phase of International Application No. PCT/JP2014/053244 filed Feb. 13, 2014, and claims priority from Japanese Applications No. 2013-033463, filed Feb. 22, 2013 and No. 2014-019902, filed Feb. 5, 2014, the disclosure of which is hereby incorporated by reference herein in its entirety.

FIELD OF TECHNOLOGY

There are many cases wherein the concentration of the dissolved substance dissolved in a liquid is measured using absorptiometry.

In the absorptiometry, for example, after the sample including a specific dissolved substance is housed inside a transparent measuring cell, a reagent is added to the sample to make a measured solution (measuring solution) in which a color is developed according to the concentration of the specific dissolved substance. Next, a light having a specific wavelength emitted from a light emitting device is transmitted to the measured solution, and one portion of the light is absorbed in the measured solution, and then, the transmitted light is received by a light receiving device, and a strength of the transmitted light at that time is measured. Next, a value of the absorbance is calculated from the strength of the transmitted light measured at that time and another measured strength of a transmitted light of, for example, a light having a specific wavelength relative to a transparent solution. Then, the concentration of the dissolved substance in the sample is calculated using the value of the absorbance, and a calibration curve created beforehand with respect to the dissolved substance, i.e., a diagram showing a relation between the value of the absorbance and a value of the concentration of the dissolved substance.

On the other hand, a light including a visible light region is transmitted to the measured solution, and within the transmitted light thereof, the light of the visible light region is divided into nearly three portions to obtain a red region component light, a green region component light, and a blue region component light, and a value of an absorbance with respect to any of the aforementioned region component lights, or a plurality of region component lights of a combination of the aforementioned region component lights, are calculated to measure the concentration of the specific dissolved substance in the sample as well (Patent Document 1).

PRIOR ART DOCUMENT

Patent Document

Patent Document 1: Japanese Unexamined Patent Application Publication No. 2010-181150

SUMMARY OF THE INVENTION

Problems to be Solved by the Invention

When the concentration of the dissolved substance in the sample is measured using the absorptiometry, however, there is a case wherein the reagent is not added in a necessary quantity to the sample due to a breakdown of a reagent pump, a blockade of a supply channel of the reagent, a deviation of a supply tube of the reagent, depletion of the reagent, or the like. This frequently occurs in a case wherein the concentration of the dissolved substance in the sample is automatically measured.

In such a case, regardless of the presence of the dissolved substance which becomes a detection object in the sample, there can occur a problem wherein the concentration of the dissolved substance is not detected at all, or the concentration of the dissolved substance is detected only for a value matching a quantity of the reagent which is less than the concentration of an actual dissolved substance so that proper concentration of the dissolved substance in the sample is not measured. Also, this problem can occur even in a case wherein the concentration of the dissolved substance is measured using the three region component lights of red, green, and blue.

In view of the above-mentioned problems, an object of the present invention is to provide a method for measuring concentration of a dissolved substance which can judge whether or not the reagent in the necessary quantity for a measurement is added to the sample when the concentration of the dissolved substance in the sample is measured using the absorbance of the three region component lights of red, green, and blue.

Means for Solving the Problems

The first invention of the present invention comprises a reagent preparation step of making a reagent including a coloring agent by adding the coloring agent, which allows a measured solution (measuring solution) to develop a color transmitting a region component light for a dissolved-substance concentration measurement selected from any of a red region component light, a green region component light, or a blue region component light obtained by transmitting a light including a visible light region to the measured solution colored by addition of a reagent to a sample, and dividing a light in the visible light region within a transmitted light thereof into roughly three portions, or selected from a plurality of the region component lights of a combination of the red, green, and blue region component lights, without being absorbed, to the reagent; a concentration measurement step of measuring concentration of a specific dissolved substance in the sample by calculating an absorbance of the region component light for the dissolved-substance concentration measurement based on the transmitted light from the measured solution to which the reagent including a coloring agent is added; and a judgement step of carrying out a judgement whether or not the reagent is added in a necessary quantity by calculating an absorbance of another region component light other than the region component light for the dissolved-substance concentration measurement based on the transmitted light from the measured solution to which the reagent including the coloring agent is added to determine a value of an absorbance of another region component light resulted only from the coloring agent, and by comparing the value of the absorbance with a value of a standard absorbance.

In the present invention, in a case wherein the measured solution colored by the dissolved substance absorbs, for example, all of three region component lights, among the three region component lights, the region component light having a linear relation between the value of the absorbance and a value of the concentration of the dissolved substance is selected as the region component light for the dissolved-substance concentration measurement. Also, any coloring agent may be used provided that the measured solution colored by the coloring agent transmits the region component light for the dissolved-substance concentration measurement without being absorbed. For example, for the coloring agent, there can be used the coloring agent allowing the measured solution to develop the same color as the region component light for the dissolved-substance concentration measurement. The measured solution colored by the coloring agent transmits the region component light for the dissolved-substance concentration measurement without being absorbed, so that the concentration of the specific dissolved substance in the sample can be easily obtained from a calibration curve created beforehand using the value of the absorbance of the region component light for the dissolved-substance concentration measurement.

Also, among the three region component lights, if the region component light for the dissolved-substance concentration measurement is, for example, the green region component light, the region component lights other than the green region component light, i.e., any one of either the red region component light or the blue region component light, for example, the red region component light transmits through the measured solution so as to show a value $A3$ of the absorbance resulted only from the coloring agent, or show a value $A1$ of the absorbance resulted from the coloring agent and the specific dissolved substance. In a case wherein the red region component light shows the absorbance resulted from the coloring agent and the specific dissolved substance, the concentration of the specific dissolved substance is known, so that a value $A2$ of the absorbance of the red region component light resulted only from the concentration of the specific dissolved substance is easily calculated from the calibration curve created beforehand. Therefore, in that case, the value $A3$ of the absorbance of the red region component light resulted only from the coloring agent is calculated using a formula of $A3=A1-A2$. The value $A3$ of the absorbance becomes a value corresponding to a quantity of the reagent added to the sample, so that in a case wherein the value $A3$ of the absorbance is smaller than a value $A0$ of the standard absorbance, the quantity of the reagent added to the sample is judged as being insufficient. Incidentally, the value of the standard absorbance represents the value of the absorbance of the region component light resulted only from the coloring agent in a case wherein the reagent in only the exactly necessary quantity is added to the sample.

As for a second invention of the present invention, in the case of the first invention, in a case wherein two kinds of the reagents are added to the sample, in the reagent preparation step, a first coloring agent, allowing the measured solution to develop a color transmitting the region component light for the dissolved-substance concentration measurement and one of the remaining region component lights among three of the region component lights without being absorbed, is added to one of the reagents to make a reagent including the first coloring agent. Also, a second coloring agent, allowing the measured solution to develop a color transmitting the region component light for the dissolved-substance concentration measurement and the other of the remaining region component lights without being absorbed, is added to the other of the reagents to make a reagent including the second coloring agent.

The coloring agent transmitting two region component lights, for example, the red region component light and the green region component light without being absorbed may be any coloring agent provided that the coloring agent allows the measured solution to develop the same color as a complementary color light of the blue region component light. Similarly, the coloring agent transmitting the red region component light and the blue region component light without being absorbed may be any coloring agent provided that the coloring agent allows the measured solution to develop the same color as a complementary color light of the green region component light, and the coloring agent transmitting the green region component light and the blue region component light without being absorbed may be any coloring agent provided that the coloring agent allows the measured solution to develop the same color as a complementary color light of the red region component light.

Therefore, as for the region component light for the dissolved-substance concentration measurement, for example, in a case wherein the red region component light is used, for the first coloring agent, for example, the coloring agent allowing the measured solution to develop the same color as the complementary color light of the green region component light is used, and for the second coloring agent, the coloring agent allowing the measured solution to develop the same color as the complementary color light of the blue region component light is used. The red region component light is not absorbed into the measured solution in which only the first coloring agent and the second coloring agent have developed a color, so that the concentration of the specific dissolved substance in the sample can be easily obtained from the calibration curve created beforehand using the value of the absorbance of the red region component light.

Also, the green region component light is not absorbed into the measured solution in which only the second coloring agent has developed a color so as to show a value $B3$ of the absorbance resulted only from the first coloring agent, or show a value $B1$ of the absorbance resulted from the first coloring agent and the specific dissolved substance. Also, the blue region component light is not absorbed into the measured solution in which only the first coloring agent has developed a color so as to show a value $C3$ of the absorbance resulted only from the second coloring agent, or show a value $C1$ of the absorbance resulted from the second coloring agent and the specific dissolved substance. In a case wherein the green region component light and the blue region component light show the absorbance resulted from the coloring agent and the specific dissolved substance, values ($B2$ and $C2$) of the absorbances of the green region component light and the blue region component light resulted only from the specific dissolved substance can be read from the calibration curve created beforehand respectively. Therefore, the value $B3$ of the absorbance of the green region component light resulted only from the first coloring agent is calculated using a formula of $B3=B1-B2$, and the value $C3$ of the absorbance of the blue region component light resulted only from the second coloring agent is calculated using a formula of $C3=C1-C2$. Then, in a case wherein the values ($B3$ and $C3$) of the absorbances are smaller than values ($B0$ and $C0$) of the standard absorbance determined with respect to each of the first reagent and the second reagent, an addition quantity of each reagent added to the sample is judged as being insufficient.

As for a third invention of the present invention, in the case of the first invention, in a case wherein the measured solution develops a color in such a way as to change the color with a change in the concentration of the specific dissolved substance, and two of the region component lights are used as the region component light for the dissolved-substance concentration measurement, in the reagent preparation step, a coloring agent, allowing the measured solution to develop a color transmitting the two of the region component lights without being absorbed, is added to the reagent to make a reagent including a coloring agent.

In the invention, in a case wherein two reagent component lights for the dissolved-substance concentration measurement are, for example, the blue region component light and the green region component light, there is used a coloring agent allowing the measured solution to develop the same color as the complementary color of the region component light other than the blue region component light and the green region component light, i.e., the red region component light. The two region component lights for the dissolved-substance concentration measurement are unaffected by the coloring agent in the measured solution, so that the concentration of the specific dissolved substance is calculated by the values of the absorbances of the two region component lights for the dissolved-substance concentration measurement. Also, the remaining red region component light shows a value of the absorbance resulted only from the coloring agent, or a value of the absorbance resulted from the coloring agent and the specific dissolved substance. Even in a case wherein the red region component light shows the value of the absorbance resulted from the coloring agent and the specific dissolved substance, the value of the absorbance resulted only from the coloring agent can be easily calculated. Therefore, the propriety of the addition quantity of the reagent added to the sample can be easily judged based on the value of the absorbance resulted only from the coloring agent of the red region component light.

As for a fourth invention of the present invention, in the case of any of the first to third inventions, in a case in which the reagent is judged as not having being added in the necessary quantity, while carrying out a re-addition of the reagent including a coloring agent, the concentration measurement step and the judgement step are repeated.

As for a fifth invention of the present invention, in the case of the fourth invention, in a case wherein the reagent is judged as not having being added in the necessary quantity even when a specific time has passed after the reagent is judged as not having being added in the necessary quantity, a warning is issued to stop a measurement in the judgement step.

As for a sixth invention of the present invention, in the case of any of the first to third inventions, in the case wherein the reagent is judged as not having being added in the necessary quantity, the warning is issued to stop the measurement in the judgement step.

Effect of the Invention

According to the aforementioned inventions, among the three region component lights, the coloring agent, allowing the measured solution to develop a color transmitting the region component light for the dissolved-substance concentration measurement without being absorbed, is added to the reagent, so that the concentration of the specific dissolved substance in the sample can be measured by the absorbance of the region component light for the dissolved-substance concentration measurement, and whether or not the reagent is added in the necessary quantity can be judged by the absorbances of the other region component lights as well. Therefore, in the invention, regardless of the addition quantity of the reagent, a concentration measurement of the dissolved substance can be always carried out properly.

BRIEF DESCRIPTION OF THE DRAWINGS

FIGS. 6($a$), 6($b$), and 6($c$) are tables showing values of the concentration of the WELLCLEAN, the absorbance of each region component light, and the like in a case wherein the measured solution is made by adding a reagent including a coloring agent to a sample solution, wherein FIG. 6($a$) is a case wherein 0.2 mL of the reagent including a coloring agent is added, FIG. 6($b$) is a case wherein 0.1 mL of the reagent including a coloring agent is added, and FIG. 6($c$) is a case wherein 0.05 mL of the reagent including a coloring agent is added.

FIG. 7 is a table showing values of the absorbance of each region component light and the like relative to an addition quantity of the reagent including a coloring agent in the case wherein the measured solution is made by adding the reagent including a coloring agent to a sample solution without the dissolved substance.

FIG. 8 is a graph showing a relation between the addition quantity of the reagent including a coloring agent and the sum of values of absorbances of a red region component light and a green region component light resulted only from the coloring agent shown in FIG. 7.

BEST MODES OF CARRYING OUT THE INVENTION

Hereinafter, embodiments of the present invention will be explained with reference to the drawings.

[Concentration Measuring Apparatus]

Figure 1:
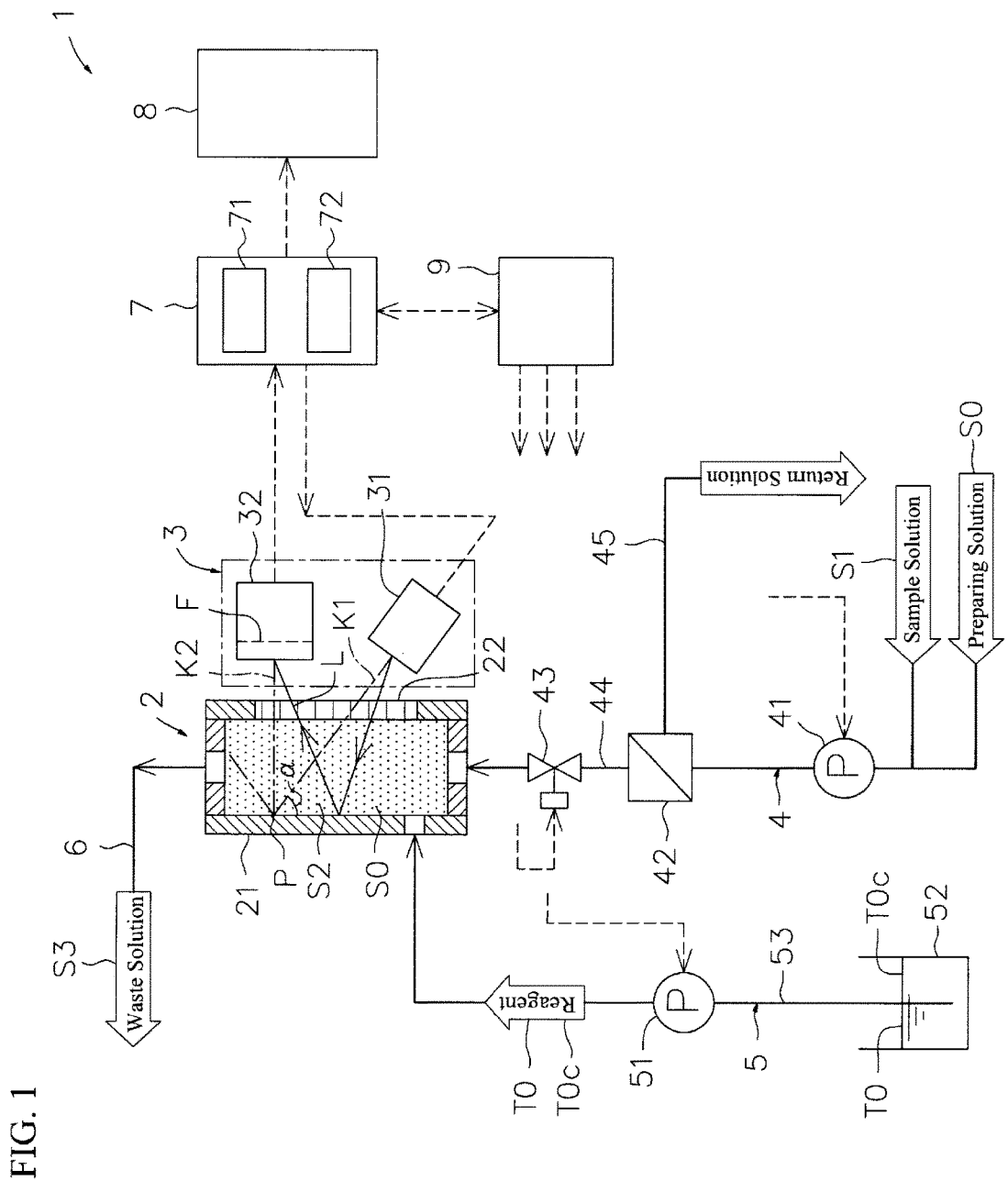
FIG. 1 is a drawing showing a concentration measuring apparatus for carrying out a method for measuring concentration of a dissolved substance according to the first embodiment of the present invention.

FIG. 1 shows a concentration measuring apparatus for carrying out the present invention.

A concentration measuring apparatus 1 automatically measures concentration of a dissolved substance such as dissolved oxygen, phosphoric acid, alkalinity component, hardness component, or silica, which dissolves in, for example, industrial water, domestic water, and the like, using an absorbance of a light.

As shown in FIG. 1, the concentration measuring apparatus 1 includes a measuring cell 2 in which a colored measured solution (colored measuring solution) S2 or a colorless preparing solution S0 are stored internally; a light receiving/emitting portion 3 attached to one lateral face of the measuring cell 2, emitting a light to a measuring cell 2 side, and receiving a light of a transmitted light from the measuring cell 2; a sample supply line 4 supplying a sample solution S1 or the preparing solution S0 including a specific dissolved substance to the measuring cell 2; a reagent supply line 5 adding a reagent T0 to the sample solution S1 inside the measuring cell 2 so that the sample solution S1 becomes the colored measured solution S2 by the specific dissolved substance; a solution discharge line 6 for discharging the measured solution S2 and the preparing solution S0 from the measuring cell 2; a computing processing apparatus 7 carrying out an input from the light receiving/emitting portion 3 and an output to the light receiving/emitting portion 3; an output apparatus 8 outputting a processed result by the computing processing apparatus 7; and a control apparatus 9 controlling equipment inside the sample supply line 4 and the reagent supply line 5. Incidentally, the sample solution S1 is colorless and transparent so as to be used as the preparing solution S0 as well.

As shown in FIG. 1, the measuring cell 2 has a box shape with a volume of 2.5 mL, and a left-lateral face portion is formed by a white reflection plate 21, and an acrylic transparent portion 22 is formed at a center portion of a right-lateral face portion facing the reflection plate 21. In the measuring cell 2, inner faces of a front face portion, a rear face portion, an upper face portion, and a lower face portion are all formed by a black plate material. The sample supply line 4 is connected to the lower face portion, the solution discharge line 6 is connected to the upper face portion, and the reagent supply line 5 is connected to the left-lateral face portion.

The light receiving/emitting portion 3 includes a light emitting device 31, a light receiving device 32, a wiring board (not shown in the drawings), and the like inside a casing where an opening is provided on the measuring cell 2 side. The light emitting device 31 emits a light (basic light) into the measuring cell 2, and transmits the light into the measured solution S2 or into the preparing solution S0. In the light emitting device 31, there is used a light source such as, for example, a light-emitting diode (LED) emitting a light (a white light) including a visible light region.

The light receiving device 32 receives a transmitted light L from the measured solution S2 or the preparing solution S0 in lights emitted from the light emitting device 31, and measures the strength of the lights with respect to the transmitted light L. The light receiving device 32 includes three photodiodes, and three color filters F, i.e., an R filter, a G filter, and a B filter respectively transmitting only a red region component light, a green region component light, or a blue region component light obtained by dividing a wavelength range of a light in the visible light region into roughly three.

Figure 2:
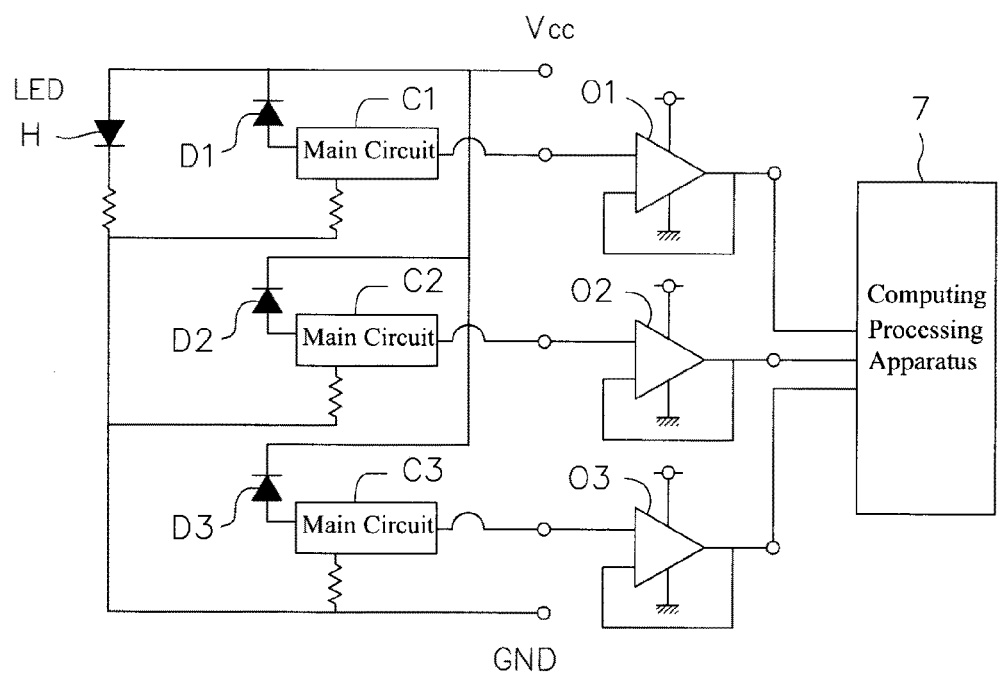
FIG. 2 is an electric wiring diagram inside a light receiving/emitting portion.

Namely, in the light receiving device 32, there is used an RGB color sensor including a photodiode D1 having the R filter, a photodiode D2 having the G filter, and a photodiode D3 having the B filter (see FIG. 2). The light receiving device 32 simultaneously measures the strengths of the respective lights of the red region component light, the green region component light, and the blue region component light (hereinafter referred to as three region component lights) transmitted through each filter within the transmitted light L transmitted through the measured solution S2. Incidentally, the R filter transmits a red light the most within the red region component light, and the G filter transmits a green light the most within the green region component light, and the B filter transmits a blue light the most within the blue region component light.

Also, as shown in FIG. 1, the light receiving device 32 is disposed on the same side as the light emitting device 31 relative to the measuring cell 2. Also, the transmitted light L in the measured solution S2 emitted from the light emitting device 31 is reflected by the reflection plate 21 facing the light emitting device 31 by sandwiching the measured solution S2, and transmits through the measured solution S2 again. Therefore, the light receiving device 32 receives the transmitted light L reflected by the reflection plate 21. In that case, the light emitting device 31 faces so that an optical axis K1 forms $\alpha$=approximately 45 degrees relative to the reflection plate 21, and the light receiving device 32 faces so that an optical axis K2 is orthogonal to the reflection plate 21. Also, the light emitting device 31 and the light receiving device 32 are positioned so that an intersection point P of the optical axis K1 of the light emitting device 31 and the reflection plate 21, and an intersection point of the optical axis K2 of the light receiving device 32 and the reflection plate 21 approximately correspond. Consequently, a primary light from the light emitting device 31 reflected by the reflection plate 21 does not reach the light receiving device 32, and the light receiving device 32 receives one portion of a reflected light by a peripheral light around the primary light from the light emitting device 31, or one portion of a light diffused by the reflection plate 21, or both of those.

FIG. 2 shows a circuit diagram inside the light receiving/emitting portion 3. In the drawing, the reference symbol D1 represents the photodiode having the R filter; the reference symbol D2 represents the photodiode having the G filter; and the reference symbol D3 represents the photodiode having the B filter. The aforementioned photodiodes are integrated to form the light receiving device 32. Also, in the drawing, the reference symbol H represents the light-emitting diode (LED) which becomes the light emitting device 31; the reference symbols C1, C2, and C3 represent main circuits for the respective photodiodes D1, D2, and D3; and the reference symbols O1, O2, and O3 represent Op-Amps (operational amplifiers) for the respective photodiodes D1, D2, and D3. A signal of a transmitted light strength of each region component light output from the light receiving device 32 is transmitted to the computing processing apparatus 7 through the Op-Amps O1, O2, and O3.

As shown in FIG. 1, the sample supply line 4 is formed by a sample pump 41; a film filter 42; an electromagnetic valve 43; a main piping 44; and a return piping 45, and supplies the sample solution S1 sampled at a specific portion to the measuring cell 2. The sample pump 41 constantly operates, and continues to supply the sample solution S1 to the measuring cell 2 side through the main piping 44. While a measurement is performed at the measuring cell 2 side, the electromagnetic valve 43 is closed, and the whole quantity of the sample solution S1 before being filtered at the film filter 42 is discharged to a return piping 45 side. When the electromagnetic valve 43 is opened, the sample solution S1 is filtered at the film filter 42, and after the sample solution S1 is supplied to the measuring cell 2, the sample solution S1 is discharged from a solution discharge line 6 side. Afterward, when the electromagnetic valve 43 is closed after a certain period of time, a fixed quantity of the filtered sample solution S1 is stored inside the measuring cell 2. Incidentally, the electromagnetic valve 43 is opened and even while the filtered sample solution S1 is being supplied to the measuring cell 2 side, a brine (a concentrated water) of a remaining portion of the sample solution S1 is discharged from the return piping 45 side as a return solution.

The reagent supply line 5 is formed by a reagent pump 51; a reagent bottle 52; and a piping 53, and supplies only a specific quantity of the reagent T0 inside the reagent bottle 52 to the measuring cell 2 by operating the reagent pump 51 only for a specific time. In that case, the reagent T0 from the reagent supply line 5 is supplied in such a way as to jet, so that the sample solution S1 and the reagent T0 are sufficiently stirred inside the measuring cell 2. Namely, inside the measuring cell 2, the measured solution S2 colored according to the concentration of the specific dissolved substance is made after a certain period of time by adding the reagent T0.

The solution discharge line 6 discharges the measured solution S2 or the preparing solution S0 (hereinafter, they are referred to as a waste solution S3), wherein the measurement is completed inside the measuring cell 2, outside the measuring cell 2. The waste solution S3 is discharged from the measuring cell 2 by supplying the sample solution S1 or the preparing solution S0 from the sample supply line 4 for a certain period of time.

The computing processing apparatus 7 is a computer operating according to a program, and includes a computing portion 71 and a memory portion 72.

The computing portion 71 calculates a time average strength with respect to each of the region component lights based on, for example, each strength signal of the three region component lights output from the light receiving device 32. Also, the computing portion 71 calculates absorbances with respect to the three region component lights using, for example, the transmitted light strength wherein one portion of the light is absorbed, and the transmitted light strength wherein the light is not absorbed, and calculates the concentration of the dissolved substance which is measured from a value of each of the absorbances with respect to the three region component lights. Furthermore, the computing portion 71 includes a function of, for example, allowing the light emitting device 31 to emit a light in a timely manner by receiving a signal of a preparation completion from the control apparatus 9, and a function of sending signals of a measurement start, a measurement completion, and a measurement stop to the control apparatus 9. The memory portion 72 stores, for example, a calibration curve showing a relation between the absorbance and the concentration of the dissolved substance with respect to a required region component light at each kind of dissolved substance. Incidentally, the computing portion 71 and the like additionally have the later-described other functions.

The output apparatus 8 displays the concentration of the specific dissolved substance and the like in the sample solution S1 calculated at the computing processing apparatus 7 on a display.

The control apparatus 9 performs an opening/closing control of the electromagnetic valve 43 of the sample supply line 4, and includes a function of discharging the waste solution S3 inside the measuring cell 2 by the sample solution S1, and storing the sample solution S1 inside the measuring cell 2. Also, the control apparatus 9 includes functions of performing an ON/OFF control of the reagent pump 51 of the reagent supply line 5, supplying the specific quantity of the reagent T0 to the sample solution S1 inside the measuring cell 2, and changing the sample solution S1 to the measured solution S2. In that case, the control apparatus 9 discharges the waste solution S3 inside the measuring cell 2 by receiving the signal of the measurement completion from the computing processing apparatus 7, and supplies the reagent T0 to the measuring cell 2, and after a certain period of time, i.e., after the measured solution S2 sufficiently colored by the reagent T0 is made, the control apparatus 9 transmits the signal of the preparation completion to the computing processing apparatus 7.

Next, a procedure of measuring the concentration of the specific dissolved substance inside the sample solution S1 using the concentration measuring apparatus 1 will be explained.

First, in a state wherein the electromagnetic valve 43 of the sample supply line 4 is closed, the sample pump 41 is operated. Thereby, the sample solution S1 supplied to the measuring cell 2 side from the main piping 44 is discharged only from the return piping 45 side without being filtered. After a certain period of time, the electromagnetic valve 43 is opened, and the filtered sample solution S1 is discharged from the solution discharge line 6 side through the measuring cell 2. Subsequently, after a certain period of time, the electromagnetic valve 43 is closed, and the sample solution S1 is discharged only from the return piping 45 side to store a specific quantity of the sample solution S1 inside the measuring cell 2.

Next, the reagent pump 51 of the reagent supply line 5 is operated only for a specific time so as to add the specific quantity of the reagent T0 to the sample solution S1 inside the measuring cell 2, and change the sample solution S1 to the measured solution S2 colored according to the concentration of the dissolved substance. When the measured solution S2 sufficiently develops a color, the light emitting device 31 of the light receiving/emitting portion 3 emits the light including the visible light region. The light reflects at the reflection plate 21 after transmitting through the measured solution S2 inside the measuring cell 2, and the light transmits through the measured solution S2 again. The transmitted light L is received by the light receiving device 32 after one portion of the light is absorbed in the measured solution S2 and the like. In that case, the transmitted light L is divided into the three region component lights, and each of the transmitted light strengths is measured. Then, a light from the light emitting device 31 is emitted repeatedly multiple times, and an average strength of each of the transmitted lights of the three region component lights is calculated.

When a measurement regarding the measured solution S2 is completed, the electromagnetic valve 43 of the sample supply line 4 is opened, and the filtered sample solution S1 is poured into the measuring cell 2 for a specific time. Thereby, the waste solution S3 inside the measuring cell 2 is discharged through the solution discharge line 6, and the inside of the measuring cell 2 is cleaned. Also, the sample solution S1 which becomes the preparing solution S0 is stored inside the measuring cell 2. Subsequently, regarding the transmitted light from the preparing solution S0, as in the case of the measured solution S2, an average strength of each of the transmitted lights of the three region component lights is calculated.

Next, based on each of the transmitted light strengths of the three region component lights regarding the measured solution S2 and the preparing solution S0, each absorbance with respect to the three region component lights is calculated. Subsequently, the concentration of the specific dissolved substance of that time is calculated from the calibration curve showing the relation between the absorbance of the region component light and the concentration of the dissolved substance, which is created with respect to a region component light for measuring the concentration of the specific dissolved substance (hereinafter, referred to as a region component light for a dissolved-substance concentration measurement) among the three region component lights. Also, the value of the concentration of the specific dissolved substance is displayed on the display of the output apparatus 8.

In a case wherein the specific dissolved substance inside the sample solution S1 is WELLCLEAN (which is a registered trademark by KURITA WATER INDUSTRIES LTD., and here, represents a dithiocarbamic acid-based heavy metal collecting agent), FIG. 3(*a*) shows how values of the absorbances of the three region component lights change at each concentration of the WELLCLEAN, and FIG. 3(*b*) shows the above as calibration curves with a graph. Among the calibration curves shown in FIG. 3(*b*), in the calibration curve related to the blue region component light, the values of the absorbances linearly change the most relative to WELLCLEAN concentrations. Therefore, it can be understood that preferably, based on an absorbance of the blue region component light as the region component light for the dissolved-substance concentration measurement, the WELLCLEAN concentration is determined.

Here, for the reagent T0 allowing the sample solution S1 including the WELLCLEAN to develop a brown color to become the measured solution S2, there is used a solution (250 mg/L) of ferrous chloride. Also, the measured solution S2 absorbs many lights in the visible light, so that any of the three region component lights is absorbed.

In the concentration measuring apparatus 1, the light from the light emitting device 31 transmits to the measured solution S2 inside the measuring cell 2 in such a way as to obliquely reciprocate, and a passing distance of the light through the measured solution S2 becomes longer so as to increase an absorbed quantity of the light into the measured solution S2 to that extent. Therefore, in the concentration measuring apparatus 1, the concentration of the dissolved substance can be accurately measured, and the measuring cell 2 can be downsized and the like.

Also, in the concentration measuring apparatus 1, the light including the visible light region from the light emitting device 31 is divided into the three region component lights at the light receiving device 32, and the absorbances of the region component lights are calculated so as to determine the concentration of the dissolved substance. Therefore, in the concentration measuring apparatus 1, even in a case wherein the concentration of any dissolved substance is measured, it is sufficient that a simple pair of light emitting device 31 and light receiving device 32 is provided, so that the measurement cost can be reduced, and the measuring apparatus can be downsized.

Incidentally, in the aforementioned explanation, the absorbances regarding all of the three region component lights are calculated; however, it is sufficient that the absorbance regarding only the region component light for the dissolved-substance concentration measurement is calculated. For example, in a case wherein the measured solution S2 develops a yellow-orange color by adding the reagent T0, it is considered that the measured solution S2 hardly absorbs the red region component light and the green region component light, and absorbs only the blue region component light which is a complementary color. Therefore, in that case, the blue region component light becomes the region component light for the dissolved-substance concentration measurement, and it is sufficient that the absorbance of only the blue region component light is calculated.

However, when the concentration of the dissolved substance is automatically measured in the concentration measuring apparatus 1 as mentioned above, in a case wherein the concentration of the dissolved substance is measured as 0 (zero), there arises a question whether or not the reagent T0 is unmistakably added to the sample solution S1. Also, in a case wherein the value of the concentration of the measured dissolved substance is small, there arises a question whether or not the reagent T0 is sufficiently added to the sample solution S1 as well. Such a non-addition or an insufficient addition of the reagent can occur by reason of clogging or coming-off of the piping 53 in the reagent supply line 5, a breakdown of the reagent pump 51, or depletion of the reagent T0 inside the reagent bottle 52. Therefore, when the concentration of the dissolved substance is measured, it becomes important that whether or not the reagent T0 is added in a necessary quantity to the sample solution S1 can be judged.

First Embodiment

Figure 4A:
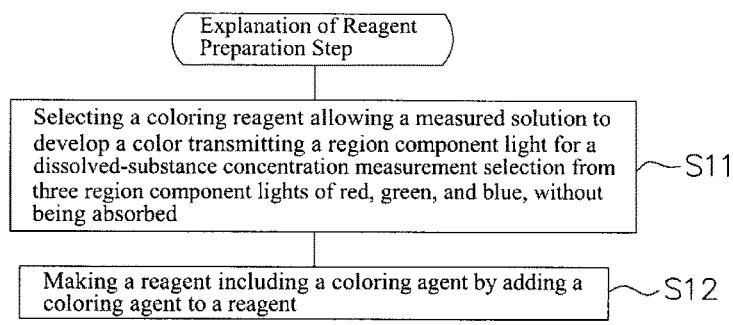
FIGS. 4($a$) and 4($b$) are flowcharts for explaining the method for measuring concentration of a dissolved substance according to the first embodiment, wherein FIG. 4($a$) explains a reagent preparation step, and FIG. 4($b$) explains one portion of a concentration measurement step, and a judgement step.

Next, the method for measuring concentration of a dissolved substance, which can judge whether or not the reagent T0 is added in the necessary quantity, according to one embodiment of the present invention will be explained with reference to FIGS. 4(*a*), 4(*b*), and 5.

The method for measuring concentration of a dissolved substance includes a reagent preparation step of making a reagent T0*c* including a coloring agent by adding a coloring agent to the reagent T0; a concentration measurement step of measuring the concentration of the specific dissolved substance in the sample solution S1 based on the transmitted light L from the measured solution S2 to which the reagent T0*c* including a coloring agent is added; and the judgement step of judging whether or not the reagent T0 is added in the necessary quantity based on the transmitted light L from the measured solution S2 to which the reagent T0*c* including a coloring agent is added.

First, the reagent preparation step will be explained.

In the reagent preparation step, the reagent T0*c* including a coloring agent is made by adding the coloring agent to the reagent T0, which allows the measured solution S2 to develop a color transmitting the region component light for the dissolved-substance concentration measurement among the three region component lights without being absorbed.

The reagent preparation step will be explained in detail according to FIG. 4(*a*).

On the assumption of the reagent preparation step, it is necessary that the region component light for the dissolved-substance concentration measurement is determined from the three region component lights. For the region component light for the dissolved-substance concentration measurement, among the three region component lights, there is selected the region component light absorbed in the measured solution S2 colored by the specific dissolved substance. Incidentally, in a case wherein any of the three region component lights is absorbed in the measured solution S2 colored by the specific dissolved substance, for example, the region component light wherein the value of the absorbance and the value of the concentration of the dissolved substance change in a linear relation is selected as the region component light for the dissolved-substance concentration measurement.

First, there is selected the coloring agent allowing the measured solution S2 to develop a color transmitting the region component light for the dissolved-substance concentration measurement without being absorbed (a step S11).

Figure 5:
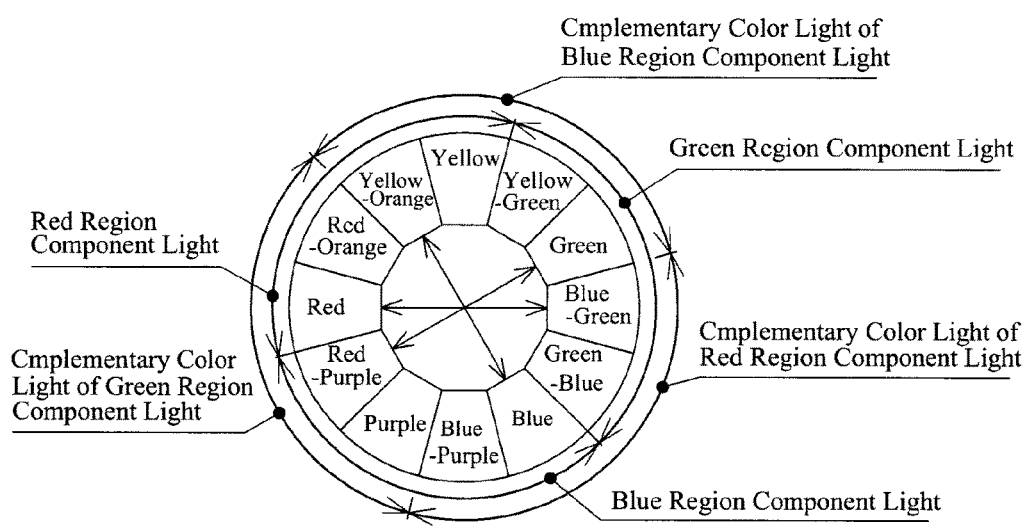
FIG. 5 is a chart showing a color circle of a visible light for explaining a coloring agent.

In order to make the explanation easier to understand, a selecting method of the coloring agent will be explained using FIG. 5. FIG. 5 shows a color circle in which twelve colors that the visible light will show are arranged in order of color changes. The color circle is divided into three, and cases of the red region component light shown by, for example, a red light, a red-orange light, a yellow-orange light, and a yellow light; the green region component light shown by, for example, a yellow-green light, a green light, a blue-green light, and a green-blue light; and the blue region component light shown by, for example, a blue light, a blue-purple light, a purple light, and a red-purple light, will be considered.

The red region component light is absorbed in the measured solution S2 which develops the same color as a complementary color thereof (any of blue-green, green-blue, blue, or blue-purple, or a mixed color of those colors). Also, the green region component light is absorbed in the measured solution S2 which develops the same color as a complementary color thereof (any of purple, red-purple, red, or red-orange, or a mixed color of those colors); and the blue region component light is absorbed in the measured solution S2 which develops the same color as a complementary color thereof (any of yellow-orange, yellow, yellow-green, or green, or a mixed color of those colors). Consequently, the red region component light transmits through the measured solution S2 developing the same color (any of red, red-orange, yellow-orange, or yellow, or a mixed color of those colors) without being absorbed. Similarly, the green region component light transmits through the measured solution S2 developing the same color (any of yellow-green, green, blue-green, or green-blue, or a mixed color of those colors) without being absorbed; and the blue region component light transmits through the measured solution S2 developing the same color (any of blue, blue-purple, purple, or red-purple, or a mixed color of those colors) without being absorbed.

Therefore, if the region component light for the dissolved-substance concentration measurement is the red region component light, the coloring agent allowing the measured solution S2 to develop the same color as the red region component light may be used for the coloring agent. Also, if the region component light for the dissolved-substance concentration measurement is the green region component light, the coloring agent allowing the measured solution S2 to develop the same color as the green region component light may be used for the coloring agent. If the region component light for the dissolved-substance concentration measurement is the blue region component light, the coloring agent allowing the measured solution S2 to develop the same color as the blue region component light may be used for the coloring agent. In that case, in a case wherein the coloring agent develops, for example, the same color (any of red, red-orange, yellow-orange, or yellow) as one color light in the red region component light, the measured solution S2 to which this coloring agent is added absorbs any one of either the green region component light or the blue region component light other than the red region component light; however, in a case wherein the coloring agent develops the same color (a mixed color of red, red-orange, yellow-orange, and yellow) as nearly all color lights in the red region component light, the measured solution S2 to which this coloring agent is added absorbs both of the green region component light and the blue region component light.

When the coloring agent is selected relative to the region component light for the dissolved-substance concentration measurement, a fixed quantity of the coloring agent is added to the specific quantity of the reagent T0 to make the reagent T0c including a coloring agent (a step S12). In that case, it is important that the concentration of the coloring agent in the reagent T0c including a coloring agent is fixed to a fixed value.

Next, the concentration measurement step will be explained.

The concentration measurement step is roughly the same as a series of operation steps explained regarding the concentration measuring apparatus 1. Namely, the concentration measurement step includes a step of making the measured solution S2 by adding the reagent T0c including a coloring agent to the sample solution S1 after the sample solution S1 is supplied to the measuring cell 2; a step of transmitting the light from the light emitting device 31 to the measured solution S2, and receiving the transmitted light L at the light receiving device 32; a step of transmitting the light from the light emitting device 31 to the preparing solution S0 after supplying the preparing solution S0 to the measuring cell 2, and receiving the transmitted light L at the light receiving device 32; a step of calculating the absorbance with respect to the region component light for the dissolved-substance concentration measurement from the transmitted lights L of the measured solution S2 and the preparing solution S0 to measure the concentration of the specific dissolved substance in the sample solution S1 from the aforementioned absorbance; and a step of making a new measured solution S2 by re-adding the insufficient reagent T0c including a coloring agent to the measured solution S2 in the measuring cell 2 in a case wherein a reagent T in a necessary quantity is not added to the sample solution S1, and calculating the absorbance with respect to the region component light for the dissolved-substance concentration measurement from the transmitted lights L of the new measured solution S2 and the preparing solution S0 to measure the concentration of the specific dissolved substance in the sample solution S1 from the aforementioned absorbance. Incidentally, the region component light for the dissolved-substance concentration measurement is unaffected by the coloring agent, so that except for a problem of an addition quantity of the reagent T0, a proper concentration of the dissolved substance is measured by the concentration measurement step.

Next, the judgement step will be explained.

The judgement step includes a step 1, a step 2, a step 3, and a step 4.

In the step 1, in the concentration measurement step, when the absorbance with respect to the region component light for the dissolved-substance concentration measurement is calculated from the transmitted lights L of the measured solution S2 and the preparing solution S0, an absorbance with respect to another region component light which is affected by the coloring agent is calculated. Then, in a case wherein the absorbance with respect to another region component light is resulted only from the coloring agent, a value thereof is A3, and in a case wherein the aforementioned absorbance is resulted from the coloring agent and the specific dissolved substance, a value thereof is A1. Incidentally, the value A3 of the absorbance corresponds to the addition quantity of the reagent T0 relative to the sample solution S1.

In the step 2, in a case wherein the value of the absorbance with respect to another region component light calculated in the step 1 is A1, i.e., in a case wherein the absorbance thereof is resulted from the coloring agent and the specific dissolved substance, a value A2 of this absorbance of another region component light resulted only from the concentration of the dissolved substance is calculated using a known calibration curve from the concentration of the dissolved substance in the sample solution S1 measured in the concentration measurement step. Then, the value A3 of the absorbance of another region component light resulted only from the coloring agent is calculated using a formula of A3=A1−A2.

In the step 3, the value A3 of an absorption of another region component light resulted only from the coloring agent, obtained in the step 1 or the step 2, is compared with the value A0 of the standard absorbance of another region component light resulted only from the coloring agent in a case wherein the reagent T0 in only the exactly necessary quantity is added to the sample solution S1. Then, if A3<A0, the reagent T0 in the necessary quantity is judged as not having being added to the sample solution S1, and if A3≥A0, the reagent T0 in the necessary quantity is judged as having being added to the sample solution S1.

In the step 4, in a case wherein the reagent T0 in the necessary quantity is judged as not having being added to the sample solution S1, the concentration measurement immediately stops, or the concentration measurement stops after being continued under certain conditions.

Figure 4B:
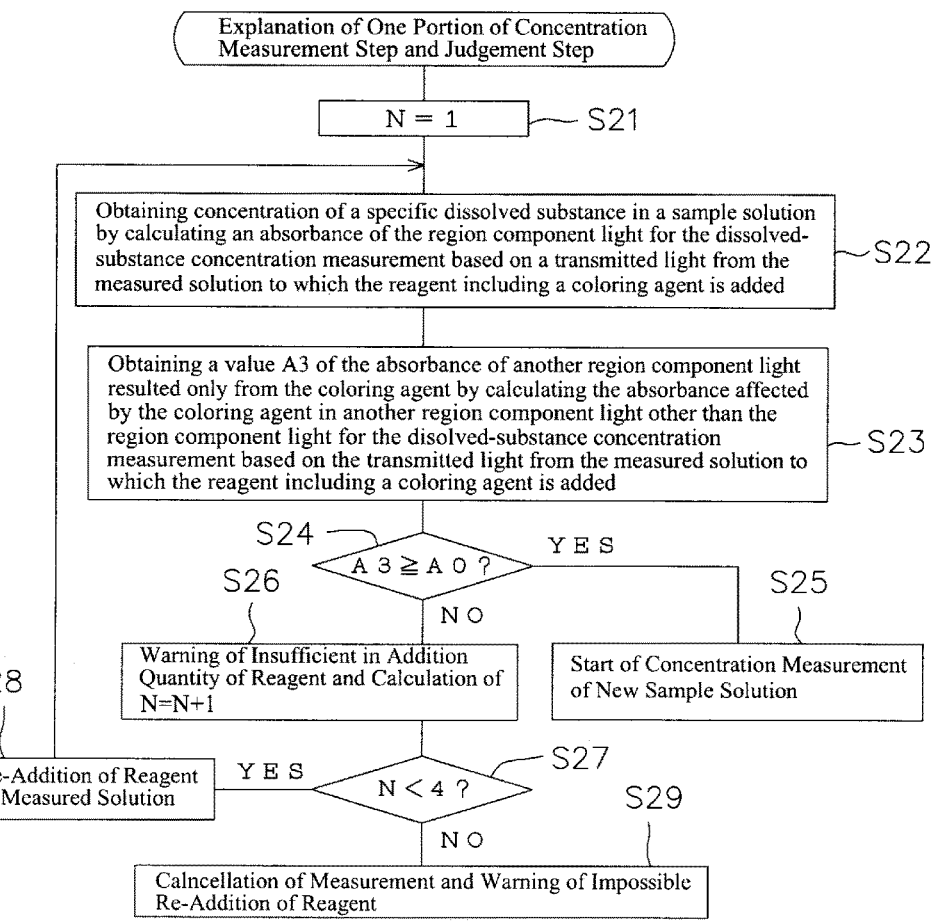

Next, one portion of the concentration measurement step and the judgement step will be explained in detail with reference to FIG. 4(b). Incidentally, FIG. 4(b) shows operations of the computing portion 71 of the computing processing apparatus 7.

First, as N=1, it is clarified that the following operation is the first operation regarding one measured solution S2 (a step S21). Subsequently, based on the transmitted light L from the measured solution S2 to which the reagent T0c including a coloring agent is added, the reagent component light for the dissolved-substance concentration measurement, for example, the absorbance of the green region component light is calculated, and based on a value of this absorbance, the concentration of the specific dissolved substance in the sample solution S1 is measured (a step S22). The region component light for the dissolved-substance concentration measurement (the green region component light) is unaffected by the coloring agent, so that the concentration of the specific dissolved substance in the sample solution S1 is easily calculated from the value of the absorbance thereof, and a calibration curve showing a relation between the concentration of the dissolved substance and the absorbance, which is created beforehand with respect to the region component light for the dissolved-substance concentration measurement (the green region component light).

Next, based on the transmitted light L from the measured solution S2 to which the reagent T0c including a coloring agent is added, there is calculated a value of an absorbance being absorbed in the measured solution S2 colored by the coloring agent among other region component lights except for the region component light for the dissolved-substance concentration measurement (the green region component light), i.e., in the red region component light or the blue region component light, for example, a value of the absorbance of the red region component light. Then, based on the value of the absorbance thereof, there is calculated the value A3 of the absorbance of the other region component light (the red region component light) resulted only from the coloring agent (a step 23). In a case wherein the other region component light (the red region component light) shows a value of the absorbance resulted only from the coloring agent, the value thereof becomes A3 without any change. Incidentally, the value A3 of the absorbance of the other region component light (the red region component light) resulted only from the coloring agent becomes a value corresponding to the addition quantity of the reagent T0 relative to the sample solution S1.

In a case wherein the other region component light (the red region component light) shows a value resulted from the coloring agent and the specific dissolved substance, it may be considered as follows. The value of the absorbance of the other region component light (the red region component light) at that time is A1. Also, the concentration of the specific dissolved substance is measured, so that from the value of the concentration of the specific dissolved substance, the value A2 of the absorbance of the other region component light (the red region component light) resulted only from the specific dissolved substance is calculated using a calibration curve of the red region component light created beforehand. Then, using the values A1 and A2 of the absorbances, the value A3 of the absorbance of the other region component light (the red region component light) resulted only from the coloring agent is calculated from the formula of A3=A1−A2.

Next, the value A3 of the absorbance obtained in the step S23 is compared with the value A0 of the standard absorbance of the other region component light (the red region component light) resulted only from the coloring agent in the case wherein the reagent T0 in only the exactly necessary quantity is added to the sample solution S1 (a step S24). In the step S24, if A3≥A0, it becomes YES, and the reagent T0 in the necessary quantity is judged as having being added, and if A3<A0, it becomes NO, and the addition quantity of the reagent T0 is judged as being insufficient.

In the step S24, if the reagent T0 in the necessary quantity is judged as having being added, the measurement of the concentration with respect to the sample solution S1 is completed, and the measurement of the concentration with respect to the new sample solution S1 starts (a step S25). Namely, in the control apparatus 9, there is issued a command of the measurement completion which discharges the preparing solution S0 in the measuring cell 2, i.e., the waste solution S3, and the new sample solution S1 is stored in the measuring cell 2, and afterward, a usual measuring operation is carried out.

Also, in the step S24, if the addition quantity of the reagent T0 is judged as being insufficient, a warning of "insufficient in addition quantity of reagent" is issued on a display of the output apparatus 8. Also, a calculation of N=N+1=2 is carried out, and it is suggested that a re-measurement can be carried out relative to the same measured solution S2 (a step S26). Subsequently, whether or not N<4 is judged (a step 27), and if N is 3 or less, i.e., if the measurement is for the third time or less, it becomes YES, so that in the control apparatus 9, there is issued a command of a re-addition of the reagent T0c including a coloring agent to the measured solution S2 in the measuring cell 2 (a step S28). Subsequently, after the reagent T0c including a coloring agent is re-added to the measured solution S2 in the measuring cell 2, the light receiving device 32 receives the transmitted light L from the light emitting device 31, and when a preparation of a calculation of the absorbance is completed, it is returned to the step S22, and again, operations on or after the step S22 are carried out. Also, in the step S24, even if the measurement is for the third time, when it becomes NO, and the addition quantity of the reagent T0 is judged as being insufficient, it becomes N=4, so that in the step S27, it becomes NO, and a warning of "impossible of re-addition of reagent" is issued to the output apparatus 8, so that the measurement stops (a step S29).

Incidentally, at the first measurement, in a case wherein the addition quantity of the reagent T0 is judged as being insufficient, a re-measurement is not carried out, and the measurement may stop as it is. Also, a standard elapsed time from the first measurement completion up to a third measurement completion is measured, and in a case wherein the addition quantity of the reagent T0 is judged as being insufficient at the first measurement, afterward, if the aforementioned standard elapsed time has passed, the measurement may be stopped.

Moreover, in a case wherein the region component light for the dissolved-substance concentration measurement is, for example, the red region component light, and the coloring agent allows the measured solution S2 to develop the same color as nearly all color lights in the red region component light, and any of the three region component lights is absorbed in the measured solution S2 resulted from the specific dissolved substance, it may be considered as follows. Namely, from the value of the concentration of the specific dissolved substance obtained from the value of the absorbance of the red region component light, values (B2 and C2) of the absorbances of other region component lights (the green region component light and the blue region component light) resulted only from the specific dissolved substance are obtained from the calibration curves, and a sum thereof (B2+C2) is calculated. Subsequently, a sum (B1+C1) of the values of the absorbances of the other region component lights (the green region component light and the blue region component light) is calculated, and a sum (B3+C3) of the values of the absorbances of the aforementioned region component lights resulted only from the coloring agent is calculated from a formula of (B1+C1)−(B2+C2). The sum (B3+C3) of the values of the absorbances becomes a value corresponding to a quantity of the reagent T0 in the measured solution S2, so that if the aforementioned value is smaller than a sum (B0+C0) of values (B0 and C0) of the standard absorbances resulted only from the coloring agent in the case wherein the reagent T0 in only the exactly necessary quantity is added to the sample solution S1, the addition quantity of the reagent T0 to the sample solution S1 is judged as being insufficient.

As mentioned above, in the method for measuring concentration of a dissolved substance, the coloring agent, allowing the measured solution S2 to develop a color transmitting the region component light for the dissolved-substance concentration measurement without being absorbed, is added to the reagent T0 to make the reagent T0c including a coloring agent, and based on the transmitted light of the measured solution S2 to which the reagent T0c including a coloring agent is added, the absorbance of the region component light for the dissolved-substance concentration measurement and the absorbances of the other region component lights resulted only from the coloring agent are calculated. Therefore, in the method for measuring concentration of a dissolved substance, when the concentration of the dissolved substance is measured, whether or not the reagent T0 in the necessary quantity is added to the sample solution S1 can be easily judged. Namely, in the method for measuring concentration of a dissolved substance, regardless of the addition quantity of the reagent T0, the proper concentration of the dissolved substance can be always measured.

Here, the computing portion 71 of the computing processing apparatus 7 includes a function of proceeding the operations explained in a flowchart in FIG. 4(b). Namely, the computing portion 71 includes a function of calculating the value of the absorbance resulted only from the coloring agent using the absorbances of the region component lights other than the region component light for the dissolved-substance concentration measurement. Also, the computing portion 71 includes a function of judging that the reagent T0 is not properly added in a case wherein the calculated value of the absorbance is small by comparing the calculated value of the absorbance with respect to the absorbance resulted only from the coloring agent, and the value of the standard absorbance, or the calculated value of the absorbance is zero (0). Moreover, in a case of being judged that the reagent T0 is not properly added, the computing portion 71 includes a function of stopping the measurement in the control apparatus 9 by issuing a warning thereof to the output apparatus 8. Also, the memory portion 72 of the computing processing apparatus 7 stores the value of the standard absorbance of the region component lights other than the region component light for the dissolved-substance concentration measurement resulted only from the coloring agent. Moreover, the memory portion 72 stores the calibration curve showing the relation between the absorbances with respect to the region component lights other than the region component light for the dissolved-substance concentration measurement, and the concentration of the dissolved substance.

Example of First Embodiment

Next, how to obtain the concentration of the dissolved substance in a case wherein the dissolved substance is the WELLCLEAN, and a method for judging whether or not the reagent T0 in the necessary quantity is added will be specifically explained with reference to FIG. 6(a) to FIG. 8.

Here, for the region component light for the dissolved-substance concentration measurement, there is used the blue region component light, and for the reagent T0, there is used the ferrous chloride solution (250 mg/L). Also, for the coloring agent, there is used a dye solution (50 mg/L) allowing the measured solution S2 to develop the same color (the mixed color of blue, blue-purple, purple, and red-purple) as nearly all color lights in the blue region component light. Therefore, the reagent T0c including a coloring agent is made by adding a fixed quantity of the dye solution to a specific quantity of the ferrous chloride solution. Moreover, a capacity of the measuring cell 2 is 2.5 mL, so that in a case wherein the reagent T0c including a coloring agent in a specific quantity is added to the measuring cell 2, the sample solution S1 comes to slightly an overflowing state, and the measured solution S2 is made only for 2.5 mL inside the measuring cell 2.

FIG. 6(a) is a case wherein only 0.2 mL of the reagent T0c including a coloring agent is added to each of six kinds of sample solutions S1 having different WELLCLEAN concentrations inside the measuring cell 2, and absorbances of measured solutions S2 thereof are examined with respect to the three region component lights.

Figures 3A, 3B:
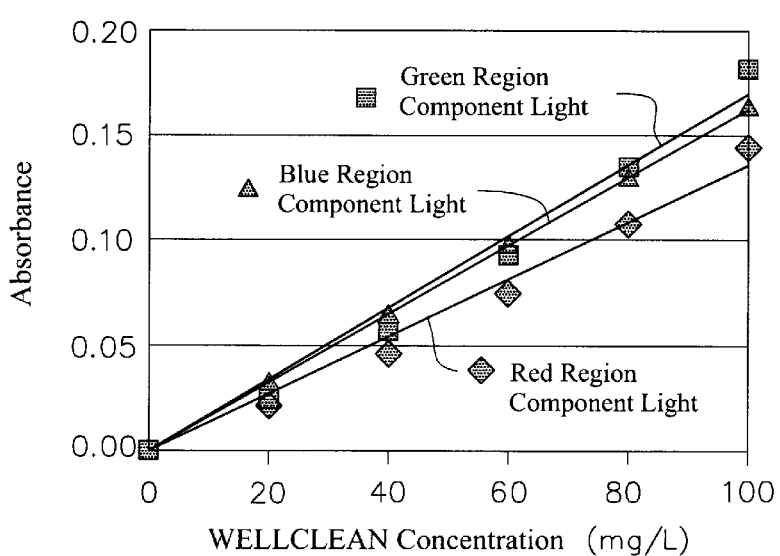
FIGS. 3($a$) and 3($b$) are charts showing values of concentration of WELLCLEAN and an absorbance of each region component light in a case wherein a measured solution is made using an ordinary reagent, wherein FIG. 3($a$) shows the above with a table, and FIG. 3($b$) shows the above with a graph.

From FIG. 6(a), values A and B of respective absorbances of the red region component light and the green region component light are affected by the WELLCLEAN and the coloring agent, so that the values thereof are larger compared with the case shown in FIG. 3(a); however, a value C of the absorbance of the blue region component light is unaffected by the coloring agent, so that the value is almost the same as the case shown in FIG. 3(a). Therefore, it can be understood that even in a case wherein the reagent T0c including a coloring agent is used, the WELLCLEAN concentration can be calculated by the absorbance of the blue region component light.

Also, as shown in FIG. 6(a), with respect to the sum of the absorbances of the red region component light and the green region component light, a value D resulted from the WELLCLEAN and the coloring agent is obtained by adding the value A of the absorbance of the red region component light to the value B of the absorbance of the green region component light, and a value E resulted only from the WELLCLEAN is obtained by adding the values of the absorbances of the red region component light and the green region component light shown in FIG. 3(a). Therefore, a sum F of the values of the absorbances of the red region component light and the blue region component light resulted only from the coloring agent can be calculated using a formula of F=D−E. The sum F of the values of the absorbances resulted only from the coloring agent corresponds to the addition quantity of the reagent T0, and by the sum F of the values of the absorbances, whether or not the reagent T0 in the necessary quantity is added to the sample solution S1 can be judged.

FIG. 6(b) shows a case wherein only 0.1 mL of the reagent T0c including a coloring agent is added to each of the sample solutions S1 having different WELLCLEAN concentrations inside the measuring cell 2, and FIG. 6(c) shows a case wherein only 0.05 mL of the reagent T0c including a coloring agent is added to each of the similar sample solutions S1. In a case wherein the quantity of the reagent T0c including a coloring agent is 0.1 mL, the sum F of the values of the absorbances of the red region component light and the green region component light resulted only from the coloring agent becomes ½ of a value in a case wherein the quantity of the reagent T0c including a coloring agent is 0.2 mL, and the quantity of the reagent T0c including a coloring agent becomes a double quantity of a value in the case of 0.05 mL of the quantity of the reagent T0c including a coloring agent. Therefrom, it can be understood that the sum F of the values of the absorbances resulted only from the coloring agent becomes a value proportional to the addition quantity of the reagent T0c including a coloring agent.

Also, in the case wherein the quantity of the reagent T0c including a coloring agent is 0.05 mL, when the WELLCLEAN concentration becomes larger than 60 mg/L, the value of the absorbance of each region component light becomes constant and comes to a value smaller than an actual value, so that it can be understood that the quantity of the reagent T0 added to the sample solution S1 is insufficient. Therefore, in a case wherein the concentration of the WELLCLEAN in the sample solution S1 can be expected to a degree of, for example, 100 mg/L, it is necessary that the addition quantity of the reagent T0c including a coloring agent is 0.1 mL or above, and the value of the standard absorbance with respect to the sum F of the values of the absorbances of the red region component light and the blue region component light resulted only from the coloring agent is, for example, 0.042 or above.

Incidentally, FIG. 7 shows a sum of the value of each absorbance of the three region component lights resulted only from the coloring agent, and the values of the absorbances of the red region component light and the green region component light resulted only from the coloring agent in a case wherein a plurality of measured solutions S2 is made by adding each 0.05 mL of the reagent T0c including a coloring agent to the sample solution S1 having 0 mg/L of the WELLCLEAN concentration inside the measuring cell 2. FIG. 8 is a graph showing a relation between the sum of the values of the absorbances of the red region component light and the green region component light resulted only from the coloring agent, and the addition quantity of the reagent T0c including a coloring agent. From the graph in FIG. 8, the sum of the values of the absorbances of the red region component light and the green region component light resulted only from the coloring agent relative to the addition quantity of the reagent T0c including a coloring agent can be understood, so that from the sum of the values of the absorbances, the value of the standard absorbance in a case wherein the reagent T0 in the necessary quantity is added can be easily determined.

Second Embodiment

Figure 9:
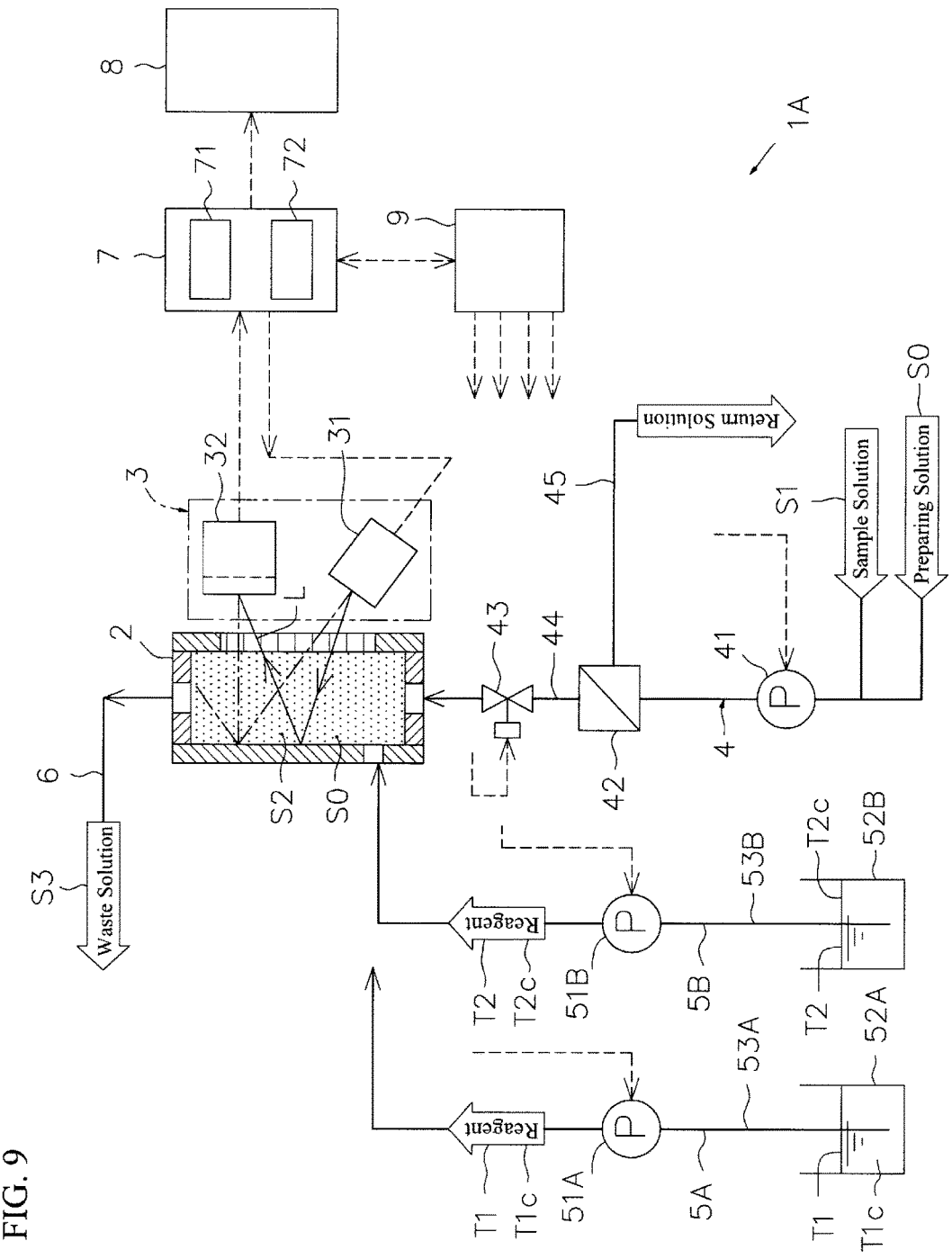
FIG. 9 is a drawing showing another concentration measuring apparatus for carrying out the method for measuring concentration of a dissolved substance according to second and third embodiments of the present invention.

Next, a case wherein the measured solution S2 is made by adding a first reagent T1 and a second reagent T2 to the sample solution S1 will be explained. Incidentally, a concentration measuring apparatus 1A in a case of two kinds of reagents is shown in FIG. 9.

In that case, in the reagent preparation step of making the reagent including a coloring agent, it is sufficient that a reagent T1c including a first coloring agent and a reagent T2c including a second coloring agent are made. The reagent T1c including the first coloring agent is made by adding a fixed quantity of the first coloring agent to a specific quantity of the first reagent T1, and the reagent T2c including the second coloring agent is made by adding a fixed quantity of the second coloring agent to a specific quantity of the second reagent T2. For the first coloring agent, there is used the coloring agent allowing the measured solution S2 to develop a color transmitting the region component light for the dissolved-substance concentration measurement among the three region component lights, for example the red region component light and the remaining region component lights, i.e., one of the green region component light or the blue region component light, for example, the green region component light without being absorbed. Also, for the second coloring agent, there is used the coloring agent allowing the measured solution S2 to develop a color transmitting the region component light for the dissolved-substance concentration measurement (the red region component light) and the other of the remaining region component lights (the blue region component light) without being absorbed.

Here, the coloring agent allowing the measured solution S2 to develop a color transmitting two region component lights without being absorbed will be specifically explained using the color circle in FIG. 5. For example, in a case wherein the two region component lights are the green region component light and the blue region component light, it is sufficient that the coloring agent develops the same color (any of blue-green, green-blue, blue, or blue-purple, or the mixed color of those colors) as the complementary color of the red region component light. Also, in a case wherein the two region component lights are the red region component light and the blue region component light, it is sufficient that the coloring agent develops the same color (any of purple, red-purple, red, or red-orange, or the mixed color of those colors) as the complementary color of the green region component light. In a case wherein the two region component lights are the red region component light and the green region component light, it is sufficient that the coloring agent develops the same color (any of yellow-orange, yellow, yellow-green, or green, or the mixed color of those colors) as the complementary color of the blue region component light.

Therefore, in a case wherein the region component light for the dissolved-substance concentration measurement is the red region component light, for example, the coloring agent allowing the measured solution S2 to develop the same color as the complementary color of the green region component light may be added to the first reagent T1 to make the reagent T1c including the first coloring agent, and the coloring agent allowing the measured solution S2 to develop the same color as the complementary color of the blue region component light may be added to the second reagent T2 to make the reagent T2c including the second coloring agent.

The region component light for the dissolved-substance concentration measurement (the red region component light) is unaffected by the first coloring agent and the second coloring agent, so that based on the absorbance of the aforementioned region component light, the concentration of the specific dissolved substance can be obtained. Also, the green region component light is affected only by the first coloring agent, and is unaffected by the second coloring agent. Therefore, for example, a value B3 of the absorbance resulted only from the first coloring agent is calculated from a value B1 of the absorbance of the green region component light showing a value of the absorbance resulted from the first coloring agent and the specific dissolved substance, and a value B2 of the absorbance of the green region component light resulted only from the dissolved substance calculated using the calibration curve from the value of the concentration of the dissolved substance, and if the value B3 of the absorbance is smaller than a value B0 of the standard absorbance, the addition quantity of the first reagent T1 is insufficient.

Moreover, the blue region component light is affected only by the second coloring agent, and is unaffected by the first coloring agent. Therefore, for example, a value C3 of the absorbance resulted only from the second coloring agent is calculated from a value C1 of the absorbance of the blue region component light showing a value of the absorbance resulted from the second coloring agent and the specific dissolved substance, and a value C2 of the absorbance of the blue region component light resulted only from the dissolved substance calculated using the calibration curve from the value of the concentration of the dissolved substance, and if the value C3 of the absorbance is smaller than a value C0 of the standard absorbance, the addition quantity of the second reagent T2 is insufficient.

Incidentally, in a case wherein the addition quantity of only one of the first reagent T1 or the second reagent T2 is judged as being insufficient, and the re-measurement is carried out, the re-measurement may be carried out by re-adding only the insufficient reagent including a coloring agent to the measured solution S2 in the measuring cell 2.

Also, the computing portion 71 of the computing processing apparatus 7 includes a function of proceeding the operation of the equipment as explained in the above. Moreover, the memory portion 72 of the computing processing apparatus 7 stores the values B0 and C0 of the standard absorbance of each region component light resulted only from the coloring agent with respect to the first reagent T1 and the second reagent T2.

Also, in the embodiment, as shown in FIG. 9, the first reagent T1 is added to the measuring cell 2 from a first reagent supply line 5A, and the second reagent T2 is added to the measuring cell 2 from a second reagent supply line 5B. Therefore, the reagent T1c including the first coloring agent is added to the measuring cell 2 from the first reagent supply line 5A as well, and the reagent T2c including the second coloring agent is added to the measuring cell 2 from the second reagent supply line 5B as well. In that case, in each of the reagent supply lines 5A and 5B, there are provided reagent pumps 51A and 51B; reagent bottles 52A and 52B; and pipings 53A and 53B, respectively, and the reagent pumps 51A and 51B are controlled by the control apparatus 9.

Third Embodiment

Next, a case wherein the measured solution S2 changes a color from the first color to the second color according to the concentration of the specific dissolved substance will be explained with reference to FIGS. 10(a) and 10(b). Incidentally, the concentration measuring apparatus 1 used in this case is the concentration measuring apparatus 1 shown in FIG. 1.

Figures 10A, 10B:
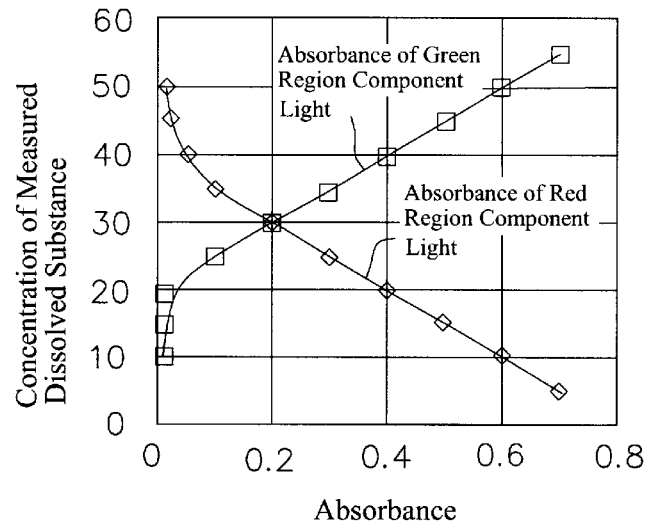
FIGS. 10($a$) and 10($b$) are tables showing the value of the absorbance of the red region component light and the value of the absorbance of the green region component light relative to the concentration of the dissolved substance in a case wherein an emitting light color of the measured solution changes by the concentration of the dissolved substance, wherein FIG. 10($a$) shows the above with a graph, and FIG. 10($b$) shows the above with a table.

FIGS. 10(a) and 10(b) show a case wherein an emitting light color of the measured solution S2 changes from a color of a complementary color light of the red region component light to a color of a complementary color light of the green region component light as the concentration of the dissolved substance rises. In that case, when the concentration of the dissolved substance starts to rise, the value of the absorbance of the green region component light rapidly rises in a curved line, and when the concentration of the dissolved substance exceeds 30, the value of the absorbance of the green region component light rises in a straight line. Also, when the concentration of the dissolved substance starts to rise, the value of the absorbance of the red region component light declines in a straight line, and when the concentration of the dissolved substance becomes 30 or less, the value of the absorbance of the red region component light gradually declines in a curved line. Therefore, the concentration of the dissolved substance is calculated based on the value of the absorbance of the red region component light when the concentration of the dissolved substance is between 0 and 30, and the concentration of the dissolved substance is calculated based on the value of the absorbance of the green region component light when the concentration of the dissolved substance exceeds 30.

In that case, for the coloring agent added to the reagent T0, there is used the coloring agent allowing the measured solution S2 to develop the same color as the complementary color of the blue region component light and transmit the red region component light and the green region component light without being absorbed. Therefore, in a case wherein the blue region component light shows, for example, the absorbance resulted from the coloring agent and the specific dissolved substance, the value of the absorbance of the blue region component light resulted only from the coloring agent is calculated, and if the value of the absorbance is smaller than the value of the standard absorbance, the addition quantity of the reagent T0 to the sample solution S1 is judged as being insufficient.

Namely, the measured solution S2 changes a color from the first color to the second color according to the concentration of the specific dissolved substance, so that in a case wherein the concentration of the dissolved substance is required to be obtained using absorbances of two region component lights for the dissolved-substance concentration measurement, the coloring agent, allowing the measured solution S2 to develop the same color as the complementary colors of the remaining region component lights, may be added to the reagent T0 to make the reagent T0c including a coloring agent. Then, the value of the absorbance resulted only from the coloring agent is calculated from the values of the absorbances of the remaining region component lights, and based on the value of the absorbance, whether or not the reagent T0 is sufficiently added to the sample solution S1 may be judged.

Incidentally, the computing portion 71 of the computing processing apparatus 7 includes the function of proceeding the operation of the equipment as explained in the above.

EXPLANATION OF SYMBOLS 1 a concentration measuring apparatus
2 a measuring cell
3 a light receiving/emitting portion
4 a sample supply line
5, 5A, and 5B reagent supply lines
6 a solution discharge line
7 a computing processing apparatus
8 an output apparatus
9 a control apparatus
31 a light emitting device
32 a light receiving device
S0 a preparing solution
S1 a sample solution (a sample)
S2 a measured solution
A0 a value of a standard absorbance of another region component light
A3 a value of an absorbance of another region component light resulted only from a coloring agent
T0, T1, and T2 reagents
T0c, T1c, and T2c reagents including a coloring agent

What is claimed is:

1. A method for measuring concentration of a dissolved substance, comprising:
adding a reagent to a sample, thereby preparing a measuring solution colored to a predetermined color based on a dissolved-substance to be measured in the sample;
irradiating a white light to the measuring solution and selecting at least one region component light capable of determining a concentration of the dissolved-substance according to an absorbance from at least one of a red region component light, a green region component light, and a blue region component light obtained by dividing a visible light in a transmitted light of the white light transmitting through the measuring solution into roughly three portions, as the region component light for a dissolved-substance concentration measurement light;
adding a coloring agent to the reagent, the coloring agent coloring the measuring solution to a color that transmits the region component light for the dissolved-substance concentration measurement without absorbing, thereby preparing the reagent containing the coloring agent;
adding the reagent containing the coloring agent to the sample, thereby preparing a colored measuring solution;
irradiating the white light to the colored measuring solution;
calculating an absorbance of the region component light for the dissolved-substance concentration measurement based on the transmitted light from the colored measuring solution, thereby measuring a concentration of the dissolved-substance in the sample;
calculating an absorbance of another region component light other than the region component light for the dissolved-substance concentration measurement based on the transmitted light from the colored measuring solution to determine an absorbance of the another region component light resulted only from the coloring agent; and
comparing a value (A3) of the absorbance of the another region component light resulted only from the coloring agent and a value (A0) of a standard absorbance of the another region component light resulted only from the coloring agent when the reagent containing the coloring agent in a predetermined amount is added to the sample in view of a case where the predetermined amount is not added for some unexpected reasons, thereby determining whether the reagent in the predetermined amount is added to the sample,
wherein, if $A3 \geq A0$, the reagent in a necessary quantity is judged as having been added, and if $A3<A0$, the reagent in an insufficient quantity is judged as having been added, and
the absorbance of the another region component light resulted only from the coloring agent corresponds to an actual amount of the reagent added to the sample.

2. The method for measuring concentration of a dissolved substance according to claim 1, wherein the reagent includes a first reagent and a second reagent,
when the first reagent and the second reagent are added to the sample, two of the red, green, and blue region component lights are different from the region component light for the dissolved-substance concentration measurement, and one of the two of the red, green, and blue region component lights is set as a first region component light and another of the two of the red, green, and blue region component lights is set as a second region component light,
the coloring agent includes a first coloring agent and a second coloring agent,
the first coloring agent colors the measuring solution to a color that transmits the first region component light and the region component light for the dissolved-substance concentration measurement without absorbing, and
the second coloring agent colors the measuring solution to a color that transmits the second region component light and the region component light for the dissolved-substance concentration measurement without absorbing.

3. The method for measuring concentration of a dissolved substance according to claim 2, further comprising
adding the first coloring agent to the first reagent, thereby preparing the first reagent containing the first coloring reagent, and
adding the second coloring agent to the second reagent, thereby preparing the second reagent containing the second coloring reagent,
wherein the second region component light is used as the another region component light when an absorbance of the another region component light resulted only from the first coloring agent is determined and the first region component light is used as the another region component light when an absorbance of the another region component light resulted only from the second coloring agent is determined.

4. The method for measuring concentration of a dissolved substance according to claim 1, wherein when the measuring solution colors according to a change in the concentration of the dissolved substance, and when the two of the red, green, and blue region component lights become the region component light for the dissolved-substance concentration measurement, the coloring agent colors the measuring solution to a color that transmits both of the region component lights for dissolved-substance concentration measurement without absorbing, and a remaining region component light becomes the another region component light.

5. The method for measuring concentration of a dissolved substance according to claim 1, further comprising re-adding the reagent containing the coloring agent to the sample while repeating the measuring of the concentration of the dissolved-substance in the sample and the determining of whether the reagent in the predetermined amount is added to the sample, when the reagent in the predetermined amount is determined as not having been added.

6. The method for measuring concentration of a dissolved substance according to claim 1, wherein the unexpected reasons include a breakdown of a reagent pump feeding the reagent, a blockade of a supply channel of the reagent, a deviation of a supply tube of the reagent, or depletion of the reagent.

* * * * *